United States Patent
Sasaki et al.

(10) Patent No.: US 7,569,718 B2
(45) Date of Patent: Aug. 4, 2009

(54) PRODUCTION PROCESS OF FLUORINATED BENZONITRILE

(75) Inventors: Toru Sasaki, Fukushima (JP); Yutaka Onishi, Kawasaki (JP); Kohei Morikawa, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 644 days.

(21) Appl. No.: 10/513,370

(22) PCT Filed: Jul. 23, 2003

(86) PCT No.: PCT/JP03/09329

§ 371 (c)(1),
(2), (4) Date: Nov. 3, 2004

(87) PCT Pub. No.: WO2004/009535

PCT Pub. Date: Jan. 29, 2004

(65) Prior Publication Data

US 2005/0131245 A1 Jun. 16, 2005

Related U.S. Application Data

(60) Provisional application No. 60/399,136, filed on Jul. 30, 2002.

(30) Foreign Application Priority Data

Jul. 24, 2002 (JP) .............................. 2002-214632

(51) Int. Cl.
*C07C 255/49* (2006.01)
(52) U.S. Cl. .................................................... 558/425
(58) Field of Classification Search ................... 558/425
See application file for complete search history.

(56) References Cited

U.S. PATENT DOCUMENTS

| 4,889,872 | A | * | 12/1989 | Naumann et al. ........... 514/531 |
| 5,215,950 | A | * | 6/1993 | Bournonville et al. ......... 502/66 |
| 6,020,517 | A |   | 2/2000 | Morinaka et al. |

FOREIGN PATENT DOCUMENTS

| DE | 37 05 224 A1 | 9/1988 |
| EP | 0164619 A | 12/1985 |
| WO | WO 98/08795 A1 | 3/1998 |

* cited by examiner

*Primary Examiner*—James O. Wilson
*Assistant Examiner*—Ebenezer Sackey
(74) *Attorney, Agent, or Firm*—Sughrue Mion, PLLC

(57) ABSTRACT

The invention enables reduction of catalyst in producing tetrafluorobenzonitrile by decyanation of one cyano group of tetrafluorodicyanobenzene by using a synthetic zeolite, particularly Zeolite 3A, 4A or 5A, in the reaction. Therefore, the invention provides an industrially useful process capable of producing tetrafluorobenzonitrile, a useful agrochemical and drug intermediate, by hydrogenolysis of tetrafluorodicyanobenzene to decyanate one cyano group with the use of catalyst in small amounts.

10 Claims, No Drawings

PRODUCTION PROCESS OF FLUORINATED BENZONITRILE

CROSS REFERENCE OF RELATED APPLICATION

This application is an application filed under 35 U.S.C. §111(a) claiming benefit pursuant to 35 U.S.C. §119(e) of the filing date of Provisional Application 60/399,136 filed on Jul. 30, 2002, pursuant to 35 U.S.C. §111(b).

FIELD OF THE INVENTION

The present invention relates to a process for producing tetrafluorobenzonitrile useful as intermediate for agrochemicals, pharmaceuticals, electrochemicals, photochemicals, speciality chemicals, speciality polymers, etc. Tetrafluorobenzonitrile is an appropriate intermediate for producing cyclopropanecarboxylic acid esters having good insecticidal activity.

BACKGROUND OF THE INVENTION

It is known that 2,2-dimethyl-3-halogenated vinyl-cyclopropanecarboxylic acid ester of benzyl alcohol substituted with 1 to 4 fluorine atoms and 0 to 2 chlorine atoms, has excellent insecticidal activity. In particular, DE-A-3705224 discloses that a cyclopropanecarboxylic acid ester of 2,3,5,6-tetrafluorobenzyl alcohol has a high insecticidal ability and that it is less toxic to mammals than a cyclopropanecarboxylic acid ester of pentafluorobenzyl alcohol and is therefore a superior insecticide.

WO 9808795 proposes a process for producing fluorinated benzyl alcohol, in which process fluorinated dicyanobenzene is hydrogenolyzed in the presence of a catalyst to hydrodecyanate only one cyano group to produce fluorinated benzonitrile and the cyano group of the fluorinated benzonitrile is converted to a hydroxymethyl group. This process is useful for the purpose of producing 2,3,5,6-tetrafluorobenzyl alcohol at high purity and in high yields.

However, the above production of fluorinated benzonitrile by hydrogenolysis of fluorinated dicyanobenzene involves so large amounts of catalyst that the cost of production is significantly affected.

OBJECT OF THE INVENTION

It is an object of the invention to provide an industrially useful process capable of producing tetrafluorobenzonitrile, a useful intermediate for agrochemicals, pharmaceuticals, electrochemicals, photochemicals, speciality chemicals, speciality polymers, etc., by hydrogenolysis of tetrafluorodicyanobenzene with the use of a catalyst in small amounts.

SUMMARY OF THE INVENTION

The present inventors have found that in carrying out hydrogenolysis of tetrafluorodicyanobenzene of the formula (1):

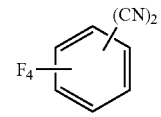

in the presence of a catalyst to hydrodecyanate only one cyano group to produce tetrafluorobenzonitrile of the formula (2)

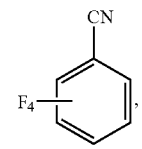

the amount of catalyst can be reduced by using a synthetic zeolite in the reaction. The present invention has been completed based on this finding.

The present invention is concerned with:

[1] A process for producing tetrafluorobenzonitrile, comprising hydrogenolysis of tetrafluorodicyanobenzene of the formula (1):

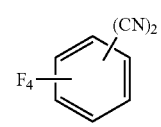

in the presence of a catalyst to hydrodecyanate only one cyano group to produce tetrafluorobenzonitrile of the formula (2):

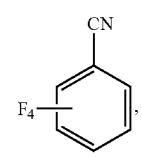

wherein a synthetic zeolite is present in the reaction system.

[2] The process of above [1], wherein the zeolite is a synthetic zeolite.

[3] The process of above [2], wherein the synthetic zeolite is at least one selected from Zeolites 3A, 4A and 5A.

[4] The process of above [2], wherein the synthetic zeolite is Zeolite 4A and/or 5A.

[5] The process of above [2], wherein the synthetic zeolite is Zeolite 5A.

[6] The process of any of above [1] to [5], wherein the catalyst is a platinum group catalyst.

[7] The process of above [6], wherein the catalyst is activated carbon-supported palladium.

[8] The process of any of above [1] to [7], wherein the water content of substances in the reaction system except the zeolite is not more than 3000 ppm of the total amount of substances in the reaction system except the zeolite.

[9] The process of any of above [1] to [8], wherein the tetrafluorodicyanobenzene is tetrafluoroterephthalonitrile and the tetrafluorobenzonitrile is 2,3,5,6-tetrafluorobenzonitrile.

BEST MODE TO CARRY OUT THE INVENTION

The present invention will be described in detail hereinafter.

The feedstock tetrafluorodicyanobenzenes of the formula (1) can be produced by known methods and are otherwise readily available in the market. Examples thereof include tetrafluorophthalonitrile, tetrafluoroisophthalonitrile, and tetrafluoroterephthalonitrile.

The hydrogenolysis of the tetrafluorodicyanobenzenes are carried out in the presence of a catalyst and a zeolite. Exemplary catalysts are platinum group metal catalysts, such metals include palladium, platinum, nickel, ruthenium and rhodium. In particular palladium is preferred. These metals can catalyze as they are or in the form of supported catalyst. Exemplary carriers for the catalyst include activated carbon, silica, and alumina. As the catalyst, activated carbon-supported palladium is preferred.

As a result of the addition of zeolite, the reaction of the invention can be nearly completed (conversion: 95% or above) with the catalyst used in amounts of 5% or less by mass, particularly even 2% or less by mass. This amount of catalyst is a mass percentage (% by mass) of the metal acting as the catalyst to the amount of feedstock tetrafluorodicyanobenzene.

Without the use of zeolite, the hydrodecyanation of tetrafluorodicyanobenzene will come to an end in the course of the reaction with such small amounts of catalyst at 5% or less by mass, so that the conversion cannot be increased. In order to raise the conversion and to achieve at least 70% yield, the catalyst should be used at 10% or more by mass, or even at 20% or more by mass based on tetrafluorodicyanobenzene.

The zeolite is preferably a synthetic zeolite. Examples of the synthetic zeolite for use in the above reaction include Zeolites 3A, 4A, 5A, 10X and 13X. Of these, Zeolites 3A, 4A and 5A are preferable, and Zeolites 4A and/or 5A are more preferable, and Zeolite 5A is particularly preferable. The synthetic zeolite is preferably used in amounts of 10% or more by mass based on the feedstock tetrafluorodicyanobenzene. There is no specific limitation on the upper limit of the zeolite amount in view of resultant effects, but the addition in excess amounts results in difficult stirring or a like problem to impede the reaction. Practically, the zeolite will be used in amounts not more than that of solvent, preferably not more than half the amount of solvent. The zeolite may be used either individually or in combination.

The solvent for use in the above reaction is not particularly limited as long as it does not influence the reaction. Examples of the solvent include aromatic hydrocarbons, such as benzene, toluene, ethylbenzene, xylene and mesitylene; aliphatic hydrocarbons, such as hexane and cyclohexane; alcohols, suchasmethanol, ethanol, 1-propanol, 2-propanol and n-butanol; and ethers, such as tetrahydrofuran, 1,4-dioxane and diethylene glycol dimethyl ether. The aromatic hydrocarbons are particularly preferred. The amount of solvent is not particularly limited within a conventional range, but is preferably equivalent to or within 50 times, more preferably from twice to twenty times that of the feedstock tetrafluorodicyanobenzene.

Since the addition of the synthetic zeolite cannot produce sufficient effects when the water content in the reaction system is large, the water content is preferably reduced prior to such addition. If the zeolite is added last, the water content before the addition is ideally not more than 3000 ppm. In this instance, the water content in the reaction system can be reduced by azeotropic distillation or the like. Since the addition sequence of the synthetic zeolite, the feedstock, etc. may be arbitrary, the total water content of the solvent, the feedstock, etc. has been ideally reduced to not more than 3000 ppm of the total amount of those substances except the synthetic zeolite when the synthetic zeolite is added to the reaction system in an earlier stage.

The reaction temperature is preferably 100° C. or above, more preferably 150° C. or above. The reaction temperature is preferably as high as possible unless boiling of the solvent, decomposition of the compound, etc. will occur at the temperature. In practice, it is difficult to raise the temperature to 350° C. or above.

The reaction can be carried out over atmospheric pressure. When the solvent of low boiling point is used, the reaction temperature should be raised by pressurization.

The reaction procedure is not particularly limited and can be a conventional one.

After the catalyst and the zeolite are separated from the reaction product by filtration, centrifugation, precipitation, etc., the resultant tetrafluorobenzonitrile can be isolated/purified by distillation or the like.

EXAMPLE

The present invention will be described by the following Examples.

The conditions for gas chromatography analysis in the Examples were as follows.

[Conditions for Gas Chromatography Analysis]

Apparatus: HP6850 (manufactured by Hewlett-Packard Company)
Column: DB-1 (produced by J&W)
0.32 mm×30 m, 1.0 µm thick
Carrier gas: He
Flow rate: 1.2 ml/min. (constant flow)
Split ratio: 50
Detector: FID
Inj. temperature: 300° C.
Det. temperature: 300° C.
Analysis temperature: 80° C. (10 min.)–10° C./min.
→200° C.–15° C./min.
→300° C. (5 min.)
Internal standard: o-dichlorobenzene Example 1

Dry tetrafluoroterephthalonitrile 51.02 g (98% pure, 50.0 g in terms of tetrafluoroterephthalonitrile), dry 5% Pd/C 1.0 g, Zeolite 4A powder 37.5 g (Molecular Sieve 4A produced by Union Showa K.K.), and toluene 200.0 g were introduced into a 500 ml stainless steel autoclave (NU-4 model produced by Nitto Koatu Co., Ltd.), and the autoclave was purged with nitrogen. Thereafter the contents were heated to 160° C. under stirring, and hydrogen pressurized at a pressure higher than that in the autoclave at the above temperature by 0.1 MPa was supplied to initiate hydrogenolysis. The rate of hydrogen absorption lowered in 2 hours after the hydrogen supply was initiated, so that the pressure in the autoclave was raised by 0.05 MPa with hydrogen. The supply of hydrogen was terminated when the hydrogen absorption was achieved at 125 mol % (based on the mol of tetrafluoroterephthalonitrile under standard conditions). The above reaction was completed in 8 hours. Cooled to room temperature, the reaction slurry was filtered, and the filtrate was analyzed with the gas chromatography analyzer. The analysis gave a conversion of 98.0% and a reaction yield of 78.0% (product: 2,3,5,6-tetrafluorobenzonitrile).

The solvent of the above reaction solution was removed by means of an evaporator, and the residue was distilled under reduced pressure to obtain 2,3,5,6-tetrafluorobenzonitrile as a fraction under 50 mmHg at 88° C.

Example 2

Water-wet tetrafluoroterephthalonitrile 56.69 g (10% water content, 98% pure, 50.0 g in terms of tetrafluoroterephthalonitrile), water-wet 5% Pd/C 2.38 g (58% water content, 1.0 g in terms of Pd), and toluene 200.0 g were introduced into a 500 ml three-necked glass flask equipped with a stirrer, a thermometer, a Claisen tube and a cooling tube. The contents were heated to distill away toluene and water together in an amount of 150.2 g. After cooling, toluene 143.0 g was added and the water content was measured to be 150 ppm. The resultant reaction solution was introduced into a 500 ml stainless steel autoclave (NU-4 model produced by Nitto Koatu Co., Ltd.), and further Zeolite 4A powder 37.5 g (Molecular Sieve 4A produced by Union Showa K.K.) was added thereto. Then the autoclave was purged with nitrogen. Thereafter the contents were heated to 160° C. under stirring, and hydrogen pressurized at a pressure higher than that in the autoclave at the above temperature by 0.1 MPa was supplied to initiate hydrogenolysis. The rate of hydrogen absorption lowered in 2 hours after the hydrogen supply was initiated, so that the pressure in the autoclave was raised by 0.05 MPa with hydrogen. The supply of hydrogen was terminated when the hydrogen absorption was achieved at 125 mol % (based on the mol of tetrafluoroterephthalonitrile under standard conditions). The above reaction was completed in 8 hours. Cooled to room temperature, the reaction slurry was filtered, and the filtrate was analyzed with the gas chromatography analyzer. The analysis gave a conversion of 96.8% and a reaction yield of 76.9% (product: 2,3,5,6-tetrafluorobenzonitrile).

Example 3

Reaction was conducted basically in the same manner as in Example 2 except that the amount of 5% Pd/C was reduced by half to 1.18 g (58% water content, 0.5 g in terms of Pd). The reaction was completed in 10 hours. The analysis gave a conversion of 96.5% and a reaction yield of 76.0% (product: 2,3,5,6-tetrafluorobenzonitrile).

Example 4

Water-wet tetrafluoroterephthalonitrile 56.69 g (10% water content, 98% pure, 50.0 g in terms of tetrafluoroterephthalonitrile), water-wet 5% Pd/C 1.18 g (58% water content, 0.5 g in terms of Pd), and toluene 200.0 g were introduced into a 500 ml three-necked glass flask equipped with a stirrer, a thermometer, a Claisen tube and a cooling tube. The contents were heated to distill away toluene and water together in an amount of 187.5 g. After cooling, toluene 187.5 g was added and the water content was measured to be 150 ppm. The resultant reaction solution was introduced into a 500 ml stainless steel autoclave (NU-4 model produced by Nitto Koatu Co., Ltd.), and further Zeolite 5A powder 45 g (Molecular Sieve 5A produced by Union Showa K.K.) was added thereto. Then the autoclave was purged with nitrogen. Thereafter the contents were heated to 160° C. under stirring, and hydrogen pressurized at a pressure higher than that in the autoclave at the above temperature by 0.1 MPa was supplied to initiate hydrogenolysis. The rate of hydrogen absorption lowered in approximately 5 hours and 30 minutes of reaction time, and the supply of hydrogen was terminated to end the reaction. The hydrogen absorption was 116 mol % (based on the mol of tetrafluoroterephthalonitrile under standard conditions). Cooled to room temperature, the reaction slurry was filtered, and the filtrate was analyzed with the gas chromatography analyzer. The analysis gave a conversion of 97.8% and a reaction yield of 84.4% (product: 2,3,5,6-tetrafluorobenzonitrile)

Example 5

Reaction was conducted basically in the same manner as in Example 4 except that the amount of 5% Pd/C was altered to 2.38 g (58% water content, 1.0 g in terms of Pd) and that the amount of the Zeolite 5A powder was altered to 37.5 g (Molecular Sieve 5A produced by Union Showa K.K.). The results were that the hydrogenolysis reaction was completed in 5 hours and 30 minutes and the hydrogen absorption was 114%. The analysis gave a conversion of 98.2% and a reaction yield of 87.5% (product: 2,3,5,6-tetrafluorobenzonitrile)

Example 6

Reaction was conducted basically in the same manner as in Example 4 except that the amount of 5% Pd/C was altered to 1.43 g (58% water content, 0.6 g in terms of Pd). The results were that the hydrogenolysis reaction was completed in 5 hours and 20 minutes and the hydrogen absorption was 121%. The analysis gave a conversion of 99.4% and a reaction yield of 86.2% (product: 2,3,5,6-tetrafluorobenzonitrile).

Example 7

Reaction was conducted basically in the same manner as in Example 4 except that the hydrogenolysis temperature was altered to 170° C. The results were that the hydrogenolysis reaction was completed in 5 hours and 30 minutes and the hydrogen absorption was 111%. The analysis gave a conversion of 99.3% and a reaction yield of 87.5% (product: 2,3,5,6-tetrafluorobenzonitrile).

Example 8

Reaction was conducted basically in the same manner as in Example 4 except that the hydrogenolysis temperature was altered to 180° C. The results were that the hydrogenolysis reaction was completed in 5 hours and 10 minutes and the hydrogen absorption was 114%. The analysis gave a conversion of 99.3% and a reaction yield of 89.1% (product: 2,3,5,6-tetrafluorobenzonitrile).

Example 9

Reaction was conducted basically in the same manner as in Example 4 except that the additional toluene was used in an amount of 147.5 g. The results were that the hydrogenolysis reaction was completed in 5 hours and 30 minutes and the hydrogen absorption was 112%. The analysis gave a conversion of 98.9% and a reaction yield of 87.0% (product: 2,3,5,6-tetrafluorobenzonitrile).

Example 10

Reaction was conducted basically in the same manner as in Example 4 except that the additional toluene was used in an amount of 107.5 g. The results were that the hydrogenolysis reaction was completed in 5 hours and 30 minutes and the hydrogen absorption was 108%. The analysis gave a conversion of 98.7% and a reaction yield of 86.5% (product: 2,3,5,6-tetrafluorobenzonitrile).

Example 11

Reaction was conducted basically in the same manner as in Example 4 except that the zeolite was changed to Zeolite MS-13X. The results were that the hydrogenolysis reaction was completed in 5 hours and 30 minutes and the hydrogen absorption was 52%. The analysis gave a conversion of 69.7% and a reaction yield of 34.7% (product: 2,3,5,6-tetrafluorobenzonitrile).

Comparative Example 1

Reaction was conducted in the same manner as in Example 1 except that no zeolite was used. The results were that the hydrogenolysis reaction was completed in 4 hours and the hydrogen absorption was 48%. The analysis gave a conversion of 55.2% and a reaction yield of 24.1% (product: 2,3,5,6-tetrafluorobenzonitrile).

Comparative Example 2

Reaction was conducted in the same manner as in Example 4 except that no zeolite was used. The results were that the hydrogenolysis reaction was completed in 3 hours and the hydrogen absorption was 42%. The analysis gave a conversion of 50.4% and a reaction yield of 20.7% (product: 2,3,5,6-tetrafluorobenzonitrile).

EFFECT OF THE INVENTION

According to the present invention, there is provided a process of producing tetrafluorobenzonitrile that is industrially advantageous.

The invention claimed is:

1. A process for producing tetrafluorobenzonitrile, comprising hydrogenolysis of tetrafluorodicyanobenzene of the formula (1):

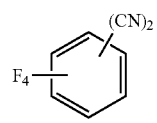

(1)

in the presence of a catalyst to hydrodecyanate only one cyano group to produce tetrafluorobenzonitrile of the formula (2):

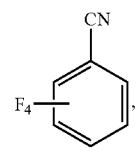

(2)

wherein a zeolite is further added to the reaction system.

2. The process as claimed in claim 1, wherein the zeolite is a synthetic zeolite.

3. The process as claimed in claim 2, wherein the synthetic zeolite is at least one selected from Zeolites 3A, 4A and 5A.

4. The process as claimed in claim 2, wherein the synthetic zeolite is Zeolite 4A and/or 5A.

5. The process as claimed in claim 2, wherein the synthetic zeolite is Zeolite 5A.

6. The process as claimed in claim 1, wherein the catalyst is a platinum group catalyst.

7. The process as claimed in claim 6, wherein the catalyst is activated carbon-supported palladium.

8. The process as claimed in any of claims 1 to 7, wherein the water content of substances in the reaction system except the zeolite is not more than 3000 ppm of the total amount of substances in the reaction system except the zeolite.

9. The process as claimed in any of claims 1 to 7, wherein the tetrafluorodicyanobenzene is tetrafluoroterephthalonitrile and the tetrafluorobenzonitrile is 2,3,5,6-tetrafluorobenzonitrile.

10. The process as claimed in claim 8, wherein the tetrafluorodicyanobenzene is tetrafluoroterephthalonitrile and the tetrafluorobenzonitrile is 2,3,5,6-tetrafluorobenzonitrile.

\* \* \* \* \*